US008626279B2

(12) United States Patent
Edvardsen et al.

(10) Patent No.: US 8,626,279 B2
(45) Date of Patent: Jan. 7, 2014

(54) METHODS FOR ESTIMATING THE RISK FOR VENTRICULAR ARRHYTHMIAS IN A SUBJECT

(75) Inventors: Thor Edvardsen, Oslo (NO); Kristina Haugaa, Oslo (NO); Jan Amlie, Oslo (NO)

(73) Assignee: Oslo Universitetssykehus HF, Oslo (NO)

( * ) Notice: Subject to any disclaimer, the term of this patent is extended or adjusted under 35 U.S.C. 154(b) by 15 days.

(21) Appl. No.: 13/032,206

(22) Filed: Feb. 22, 2011

(65) Prior Publication Data

US 2011/0263996 A1 Oct. 27, 2011

Related U.S. Application Data

(60) Provisional application No. 61/306,678, filed on Feb. 22, 2010.

(51) Int. Cl.
*A61B 5/04* (2006.01)
(52) U.S. Cl.
USPC .......................................................... 600/515
(58) Field of Classification Search
USPC ........... 600/515, 424, 411, 407, 508; 382/131
See application file for complete search history.

(56) References Cited

U.S. PATENT DOCUMENTS

| 2008/0260230 A1* | 10/2008 | Gotardo et al. | 382/131 |
| 2010/0049063 A1* | 2/2010 | Dobak, III | 600/508 |
| 2010/0280355 A1* | 11/2010 | Grimm et al. | 600/411 |

OTHER PUBLICATIONS

Buxton, Alfred E. et al., "Limitations of Ejection Fraction for Prediction of Sudden Death Risk in Patients With Coronary Artery Disease" Journal of the American College of Cardiology, 2007, pp. 1150-1157, vol. 50, No. 12.
Edvardsen, Thor et al., "Quantitative Assessment of Intrinsic Regional Myocardial Deformation by Doppler Strain Rate Echocardiography in Humans" Circulation, 2002, pp. 50-56, vol. 106.
Greenberg, H. et al., "Left ventricular dysfunction after acute myocardial infarction: results of a prospective multicenter study" J. Am. Coll. Cardio., Nov. 1984, pp. 867-874, vol. 5.
Haugaa, Kristina Hermann et al., "Left ventricular mechanical dispersion by tissue Doppler imaging: a novel approach for identifying high-risk individuals with long QT syndrome" European Heart Journal, 2009, pp. 330-337, vol. 30.
MERIT-HF Study Group "Effect of metoprolol CR/XL in chronic heart failure: Metoprolol CR/XL Randomised Intervention Trial in Congestive Heart Failure" The Lancet, Jun. 12, 1999, pp. 2001-2007, vol. 353.
Moss, Arthur J. et al., "Prophylactic Implantation of a Defibrillator in Patients with Myocardial Infarction and Reduced Ejection Fraction" The New England Journal of Medicine, Mar. 21, 2002, pp. 877-883, vol. 346, No. 12.
Nagueh, Sherif F. "Mechanical Dyssynchrony in Congestive Heart Failure" Journal of the American College of Cardiology, 2008, pp. 18-22, vol. 51, No. 1.

(Continued)

*Primary Examiner* — Robert N Wieland
(74) *Attorney, Agent, or Firm* — Knobbe Martens Olson & Bear LLP

(57) ABSTRACT

The present invention relates to methods for predicting the risk for ventricular arrhythmias in a subject who has previously suffered a myocardial infarction (MI) or suffers from a primary cardiomyopathy, said method comprising measuring the myocardial mechanical dispersion in said subject and estimating the risk for ventricular arrhythmias based on said measurements. Similar the invention relates to a method for evaluating whether a subject is a candidate for implantable cardioverter-defibrillator (ICD) therapy.

19 Claims, 10 Drawing Sheets

(56) References Cited

OTHER PUBLICATIONS

Pirat, Bahar et al., "A Novel Feature-Tracking Echocardiographic Method for the Quantitation of Regional Myocardial Functions" Journal of the American College of Cardiology, 2008, pp. 651-659, vol. 51, No. 6.

Quiñones, Miguel A. et al., "Echocardiographic Predictors of Clinical Outcome in Patients With Left Ventricular Dysfunction Enrolled in the SOLVD Registry and Trials: Significance of Left Ventricular Hypertrophy" Journal of the American College of Cardiology, 2000, pp. 1237-1244, vol. 35, No. 5.

Reisner, Shimon A. et al., "Global Longitudinal Strain: A Novel Index of Left Ventricular Systolic Function" Journal of the American Society of Echocardiography, 2004, pp. 630-633, vol. 17, No. 6.

Schmidt, André et al., "Infarct Tissue Heterogeneity by Magnetic Resonance Imaging Identifies Enhanced Cardiac Arrhythmia Susceptibility in Patients With Left Ventricular Dysfunction" Circulation, 2007, pp. 2006-2014, vol. 115.

Spragg, David D. et al., "Abnormal conduction and repolarization in late-activated myocardium of dyssynchronously contracting hearts" Cardiovascular Research, 2005, pp. 77-86, vol. 67.

Vartdal, Trond et al., "Early Prediction in Infarct Size by Strain Doppler Echocardiography After Coronary Reperfusion" Journal of the American College of Cardiology, 2007, pp. 1715-1721, vol. 49, No. 16.

Vassallo, Joseph A. et al., "Nonuniform Recovery of Excitability in the Left Ventricle" Circulation, 1988, pp. 1365-1372, vol. 78.

Zareba, W. et al., "Dispersion of ventricular repolarization and arrhythmic cardiac death in coronary artery disease" Am. J. Cardiol., Sep. 15, 1994, pp. 550-553, vol. 74, No. 6.

Zipes, Douglas P. et al., "Sudden Cardiac Death" Circulation, 1998, pp. 2334-2351, vol. 98.

* cited by examiner

Table 1
Clinical characteristics in 85 patients with ICD, 20 control patients with prior MI and 23 healthy individuals

| | Healthy Individuals n=23 | Control patients with prior MI n=20 | ICD patients without follow up arrhythmic events n=47 | ICD patients with follow up arrhythmic events n=38 | P-value |
|---|---|---|---|---|---|
| Age (years) | 62±10 | 62±13 | 62±10 | 65±10 | 0.53 |
| Heart rate (bpm) | 65±11 | 64±12 | 68±13 | 63±13 | 0.36 |
| Women (n) | 7 (30%) | 3 (15%) | 10 (21%) | 3 (8%) | 0.04 |
| Time from MI (years) | | 4.5 (2.0,30.0) | 6.2 (0.4,29.9) | 5.9 (0.6,35.8) | 0.98 |
| QRS duration (ms) | | 100±15 | 100±15 | 100±25 | 0.93 |
| QTc (ms) | | 420±25 | 450±45 | 440±40 | 0.23 |
| Amiodarone (n) | | 0 | 10 (21%) | 8 (21%) | 0.07 |
| Beta blocker (n) | | 19 (95%) | 43 (91%) | 35 (92%) | 0.93 |
| ACE-/ ATII-inhib (n) | | 14 (70%) | 40 (85%) | 32 (84%) | 0.42 |
| Revascularization therapy (n) | | 13 (65%) | 29 (62%) | 25 (66%) | 0.92 |
| ICD primary prevention (n) | | | 24 (51%) | 20 (53%) | 0.89 |
| ICD secondary prevention (n) | | | 23 (49%) | 18 (47%) | 0.89 |

Mean±SD, Median (range). Right column shows P-values for ANOVA F-test, Kruskal Wallis test and Chi-square test, bpm=beats per minute. MI=myocardial infarction

Fig. 5

Table 2
Echocardiographic findings in 85 patients with ICD, 20 control patients with prior MI and 23 healthy individuals

| | Healthy individuals n=23 | Control patients with prior MI n=20 | ICD patients without follow up arrhythmic events n=47 | ICD patients with follow up arrhythmic events n=38 | P-value |
|---|---|---|---|---|---|
| EF (%) | 62±7 | 55±9 | 34±11# | 35±9# | <0.001 |
| EF > 35% (n) | 23 (100%) | 20 (100%) | 21 (45%)# | 22 (58%)# | <0.001 |
| LVEDV (ml) | 107±28 | 110±26 | 188±68# | 202±86# | <0.001 |
| LVESV (ml) | 42±13 | 51±19 | 126±59# | 132±66# | <0.001 |
| Global strain (%) | -21.6±2.8 | -15.9±2.5† | -11.2±4.0# | -10.0±3.7# | <0.001 |
| Mechanical dispersion (ms) | 22±10 | 45±15* | 56±13* | 85±29† | <0.001 |
| Delta contraction duration (ms) | 70±33 | 145±55* | 195±65* | 335±115† | <0.001 |

Fig. 6

Table 3
Predictors of arrhythmias during follow up that require appropriate ICD therapy in a total of 85 post-MI patients with ICD by Cox regression analysis

| Variable | Primary prevention Patients n=44 | | Secondary prevention patients n=41 | |
|---|---|---|---|---|
| | HR (95% CI) | p | HR (95% CI) | p |
| Univariate analyses | | | | |
| Age (per 5 years increase) | 1.12 (0.90-1.40) | 0.30 | 1.14 (0.85-1.48) | 0.33 |
| Gender (man vs. woman) | 1.04 (0.23-4.58) | 0.95 | 5.42 (0.72-40.8) | 0.19 |
| Heart rate (per 5 bpm increase) | 0.98 (0.77-1.19) | 0.89 | 0.90 (0.74-1.08) | 0.25 |
| QRS (per 10 ms increase) | 0.78 (0.50-1.15) | 0.20 | 0.97 (0.76-1.24) | 0.78 |
| QTc (per 10 ms increase) | 1.02 (0.94-1.10) | 0.71 | 0.95 (0.79-1.14) | 0.56 |
| Amiodarone therapy (yes vs. no) | 1.54 (0.35-6.86) | 0.57 | 1.06 (0.40-2.86) | 0.91 |
| Revascularization therapy (yes vs. no) | 1.01 (0.39-2.62) | 0.97 | 0.97 (0.36-2.59) | 0.95 |
| NsVT / inducible VT (yes vs. no) | 2.62 (0.59-11.56) | 0.21 | | |
| EF (per 5% increase) | 0.80 (0.59-1.08) | 0.15 | 1.13 (0.90-1.42) | 0.30 |
| Global strain (per 1% increase) | 0.84 (0.71-0.99) | 0.03 | 0.98 (0.85-1.12) | 0.98 |
| Mechanical dispersion (per 10 ms increase) | 1.25 (1.10-1.43) | <0.01 | 1.30 (1.09-1.55) | <0.01 |
| Delta contraction duration (per 10 ms increase) | 1.05 (1.01-1.08) | <0.01 | 1.06 (1.02-1.10) | <0.01 |
| Multivariate analyses | | | | |
| Age (per 5 years increase) | 1.23 (0.93-1.55) | 0.15 | 1.23 (0.94-1.59) | 0.14 |
| Gender (man vs. woman) | 0.92 (0.18-4.78) | 0.92 | 3.80 (0.50-29.44) | 0.20 |
| EF (per 5% increase) | 0.96 (0.56-1.45) | 0.68 | 1.08 (0.83-1.40) | 0.51 |
| Global strain (per 1% increase) | 0.92 (0.76-1.11) | 0.37 | | |
| Mechanical dispersion (per 10 ms increase) | 1.24 (1.07-1.43) | <0.01 | 1.31 (1.08-1.58) | <0.01 |

HR = hazard ratio, NsVT = non sustained ventricular tachycardia, Inducible VT = Inducible ventricular tachycardia in electrophysiologic study

Fig. 7

Table 4
Separate results from 42 ICD patients with EF<35% and 43 ICD patients with EF>35%

| | EF<35% | | | EF>35% | | |
|---|---|---|---|---|---|---|
| | Without follow up arrhythmic events N=26 | With follow up arrhythmic events N=16 | P | Without follow up arrhythmic events N=21 | With follow up arrhythmic events N=22 | P |
| Age (years) | 60±9 | 64±8 | 0.52 | 64±10 | 67±11 | 0.32 |
| EF (%) | 27±5 | 27±5 | 0.99 | 44±8 | 41±5 | 0.23 |
| Global strain (%) | -8.9±2.2 | -7.2±3.0 | 0.04 | -14.0±4.0 | -12.0±3.0 | 0.05 |
| Mechanical dispersion (ms) | 52±13 | 95±31 | <0.001 | 61±12 | 80±27 | 0.01 |
| Delta contraction duration (ms) | 170±40 | 340±120 | <0.001 | 225±80 | 280±110 | 0.06 |
| QRS duration (ms) | 104±14 | 107±26 | 0.88 | 95±13 | 101±28 | 0.49 |
| ICD secondary prevention (n) | 12(46%) | 3(19%) | 0.07 | 11(52%) | 15(68%) | 0.29 |
| ICD primary prevention (n) | 14(54%) | 13(81%) | 0.07 | 10(48%) | 7(32%) | 0.29 |

Fig. 8

METHODS FOR ESTIMATING THE RISK FOR VENTRICULAR ARRHYTHMIAS IN A SUBJECT

CROSS-REFERENCE TO RELATED APPLICATION

This application is a non-provisional of and claims the benefit of priority to U.S. provisional Patent Application Ser. No. 61/306,678, filed on Feb. 22, 2010, the disclosures of which are hereby expressly incorporated by reference in their entireties.

FIELD OF THE INVENTION

The present invention relates to methods for estimating the risk for ventricular arrhythmias in a subject. In particular the present invention relates to methods for estimating the risk for ventricular arrhythmias in a subject who has previously suffered myocardial infarction and in subjects with primary cardiomyopathies.

BACKGROUND OF THE INVENTION

The implantable cardioverter-defibrillator (ICD) represents an important innovation in the treatment of sudden cardiac death, but significant questions remain unsolved. Currently, left ventricular ejection fraction (EF) is the primary parameter used to select patients for ICD therapy. Impaired EF is shown to be a marker of increased cardiovascular mortality and sudden cardiac death, but has relatively low sensitivity to detect arrhythmic risk. There is emerging awareness of the limitations in using EF as the main risk stratification tool for ICD therapy. Sudden cardiac arrest accounts for a smaller proportion of deaths in patients with lowest EF than in patients with relatively preserved ventricular function. A variety of diagnostic tests have been proposed to improve the accuracy for selection of patients who need ICD therapy. Currently available data, however, do not support additional risk-stratification methods for selection of patients for ICD therapy.

The presence of myocardial scar forms the substrate for malignant arrhythmias. Heterogeneity in scar tissue create areas of slow conduction that generate the substrate for ventricular arrhythmia post-MI and in selected primary cardiomyopathies. Electrical dispersion, including both activation time and refractoriness, in heterogenic tissue is a known arrhythmogenic factor. Electrical abnormalities may lead to distorted myocardial function. Therefore, regional differences in electrical properties may cause heterogeneity of myocardial contraction and may be recognized as mechanical dispersion. Subtle contraction heterogeneity can be demonstrated by myocardial strain echocardiography. Myocardial strain echocardiography can accurately quantify timing and regional myocardial function. It has recently demonstrated heterogeneity of systolic contraction by echocardiography as mechanical dispersion, assumingly as a consequence of electrical dispersion in patients with long QT syndrome (LQTS) (Haugaa K H et al; Left ventricular mechanical dispersion by tissue Doppler imaging: a novel approach for identifying high-risk individuals with long QT syndrome. Eur Heart J 2009;30:330-7). LQTS is an inherited cardiac arrhythmic disease affecting children and young individuals with no visible structural alterations in the myocardium. Ion channel defects in LQTS result in dispersed electrical repolarization and it was showed that mechanical dispersion was present in these patients along with normal myocardial shortening. In these patients, mechanical dispersion was associated with ventricular arrhythmias.

The mechanism for electrical dispersion in post-MI patients and patients with primary cardiomyopathies, however, is different from LQTS patients. In post-MI patients and in patients with primary cardiomyopathies, delayed start of ventricular activation in scarred and heterogeneous myocardium leads to a dispersed recovery of excitability, resulting in dispersed electrical repolarization.

Hence, an improved method for estimating the risk for ventricular arrhythmias in a subject would be advantageous, and in particular a more efficient and/or reliable method for estimating the risk for ventricular arrhythmias in a subject who has previously suffered myocardial infarction would be advantageous.

SUMMARY OF THE INVENTION

We hypothesized that post-MI patients and subjects with primary cardiomyopathies being at risk for cardiac arrhythmias have increased myocardial mechanical dispersion due to tissue heterogeneity between infarcted and normal myocardium. We aimed to investigate if mechanical dispersion and myocardial function by strain echocardiography in post-MI patients may serve as risk markers for cardiac arrhythmias.

Thus, an object of the present invention relates to improved methods for estimating the risk for ventricular arrhythmias in a subject.

In particular, it is an object of the present invention to provide a method that solves the above mentioned problems of the prior art with reliable methods for estimating the risk for ventricular arrhythmias in a subject who has previously suffered myocardial infarction or in a subject who suffers from a primary cardiomyopathy. Thus, one aspect of the invention relates to a method for predicting the risk for ventricular arrhythmias in a subject who has previously suffered a myocardial infarction or in a subject who suffers from a primary cardiomyopathy, said method comprising measuring a myocardial mechanical dispersion in said subject, and estimating a risk for ventricular arrhythmias by comparing said measured myocardial mechanical dispersion to a cut-off value.

Thus, the method may be considered a noninvasive technique for assessing regional heterogeneity in ventricular contraction which might be used to risk stratify a subject who have previously suffered myocardial infarction or a subject who suffers from a primary cardiomyopathy.

Another aspect of the present invention relates to a method for estimating whether a subject who has previously suffered a myocardial infarction or evaluating whether a subject who suffers from a primary cardiomyopathy is a candidate for implantable cardioverter-defibrillator (ICD) therapy, said method comprising measuring a myocardial mechanical dispersion in said subject, and estimating a risk for ventricular arrhythmias by comparing said measured myocardial mechanical dispersion to a cut-off value.

Yet another aspect of the present invention is to provide the use of an echocardiography system on a subject who has previously suffered a myocardial infarction (MI) or on a subject who suffers from a primary cardiomyopathy for determining whether the subject is a candidate for implantable cardioverter-defibrillator (ICD) therapy, comprising the use of the apparatus for measurement of strain in a plurality of left ventricular segments of the subject, and for determining a measure of mechanical myocardial dispersion from the measured strains.

Global strain, mechanical dispersion and delta contraction duration.

Figure 1:
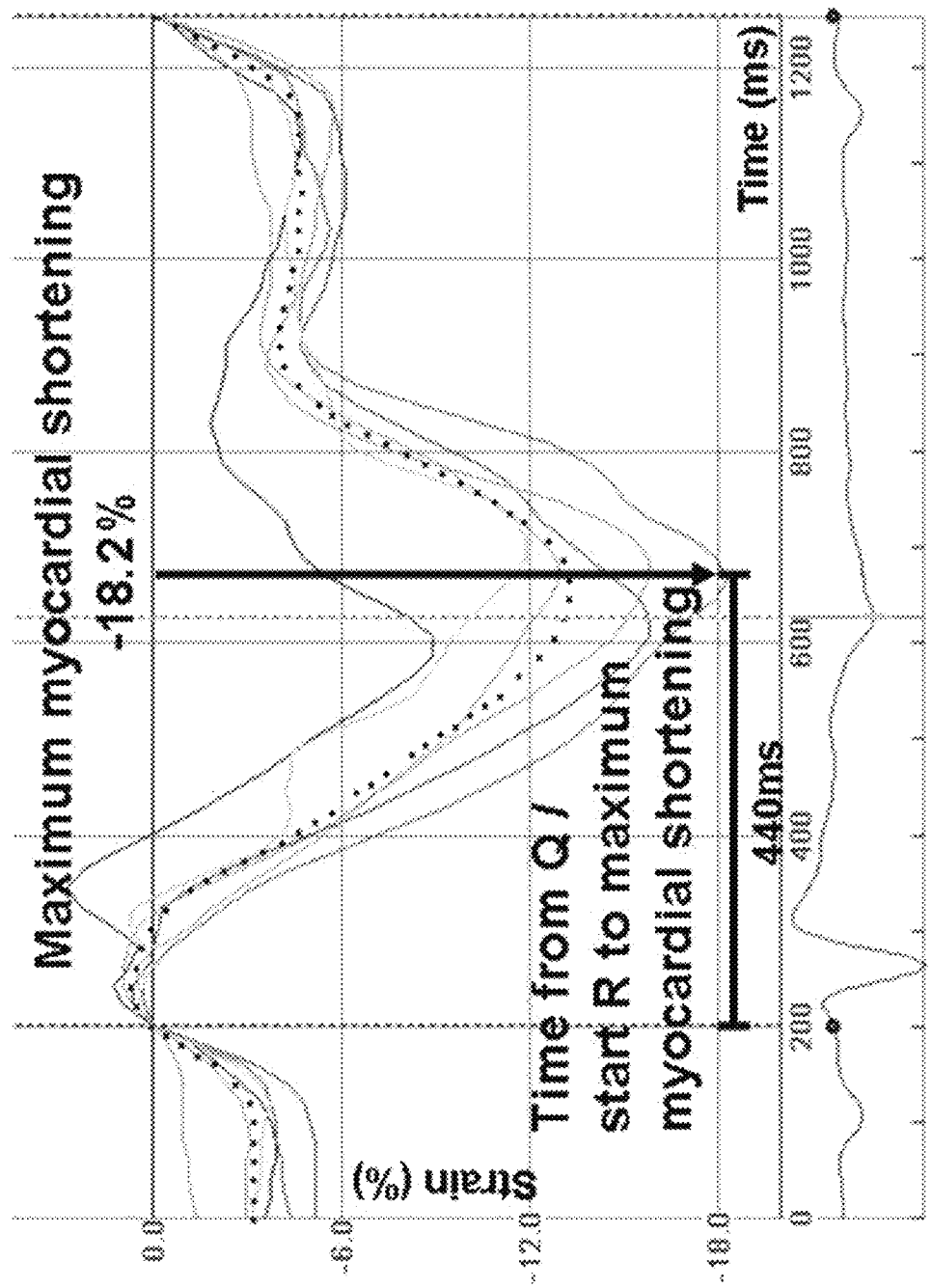
FIG. 1

FIG. 1 shows speckle tracking longitudinal strain curves in 4-chamber view from a post-MI patient. Maximum myocardial shortening in one of the segments is indicated (black arrow) and time from ECG onset Q/onset R wave to maximum myocardial shortening in this segment is indicated by a time line.

Global strain: average value of maximum myocardial shortening in 16 LV segments.

Mechanical dispersion: Standard deviation of time interval from ECG onset Q/onset R wave to maximum myocardial shortening in 16 LV segments.

Delta contraction duration: Difference between segments with longest and shortest time interval from ECG onset Q/onset R wave to maximum myocardial shortening.

FIG. 2

Figure 2:
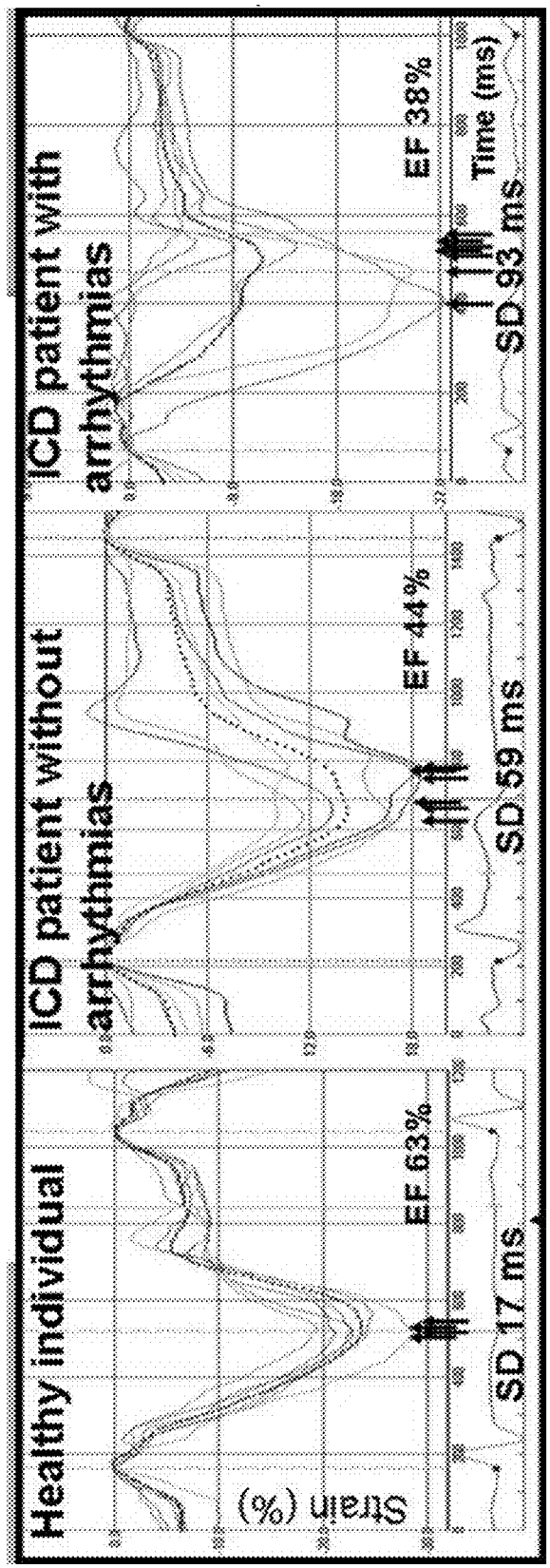

FIG. 2 shows mechanical dispersion by strain echocardiography in a healthy individual and ICD patients without and with follow up arrhythmias.

Speckle tracking longitudinal strain curves in 4-chamber view from a healthy individual (left panel), a post-MI ICD patient without arrhythmic events (center panel) and a post-MI ICD patient with recurrent arrhythmias (right panel). White arrows indicate timing of maximum myocardial shortening in each segment. Myocardial shortening is reduced in the ICD patients and the timing of shortening is dispersed compared to the healthy individual. The dotted line represents the average myocardial shortening for each individual. SD=standard deviation of time to maximum myocardial shortening.

FIG. 3

Kaplan Meier arrhythmia free survival in 85 post-MI patients with ICD. Kaplan Meier plot demonstrates arrhythmia event free survival in 85 post-MI ICD patients. Mechanical dispersion is defined as the standard deviation of time to maximum myocardial shortening in a 16 segment LV model and reflects the heterogeneity of myocardial contraction throughout the ventricle. Patients with mechanical dispersion >70 ms show higher arrhythmia event rate.

FIG. 4

ROC curve for the ability of mechanical dispersion to identify follow up arrhythmic events in 85 post-MI ICD patients.

The cut-off value for mechanical dispersion of 41 ms provided 100% sensitivity and 88 ms provided 100% specificity in predicting arrhythmic events. Optimal cut-off value was 70ms with a sensitivity of 65% and specificity of 92% in predicting arrhythmic events.

Area under the curve: 0.84 (95% CI 0.75-0.92).

FIG. 5

FIG. 5 (table 1) shows clinical characteristics in 85 patients with ICD, 20 control patients with prior MI and 23 healthy individuals. Mean±SD, Median (range). Right column shows P-values for ANOVA F-test, Kruskal Wallis test and Chi-square test, bpm=beats per minute, MI=myocardial infarction.

FIG. 6

FIG. 6 (table 2) shows echocardiographic findings in 85 patients with ICD 20 control patients with prior MI and 23 healthy individuals. Mean±SD. Right column shows P-values for ANOVA F-test and Chi-square test. Flags for significance are obtained with the Bonferroni post hoc test. *P<0.001 compared to healthy individuals

P<0.05 compared to healthy individuals and control patients with prior MI †P<0.001 compared to all other groups. EF=ejection fraction; LVEDV=left ventricular end diastolic volume; LVESV =left ventricular end systolic volume; Mechanical Dispersion=standard deviation of time interval from ECG onset Q/onset R wave to maximum myocardial shortening in 16 LV segments; Delta contraction duration=difference between longest and shortest duration of time from ECG onset Q/onset R to maximum myocardial shortening in a 16 segment model.

FIG. 7

FIG. 7 (table 3) shows predictors of arrhythmias during follow up that require appropriate ICD therapy in a total of 85 post-MI patients with ICD by Cox regression analysis. HR=hazard ratio, NsVT=non sustained ventricular tachycardia, Inducible VT=Inducible ventricular tachycardia in electrophysiologic study

FIG. 8

FIG. 8 (table 4) shows separate results from 42 ICD patients with EF<35% and 43 ICD patients with EF>35%. Mean±SD. P-values for ANOVA F-test. MI=myocardial infarction; EF=ejection fraction; Mechanical dispersion=standard deviation of time interval from onset Q/onset R wave to maximum myocardial shortening in 16 LV segments; Delta contraction duration=difference between longest and shortest duration of time from ECG onset Q/onset R to maximum myocardial shortening in a 16 segment model.

FIG. 9

Figure 9:
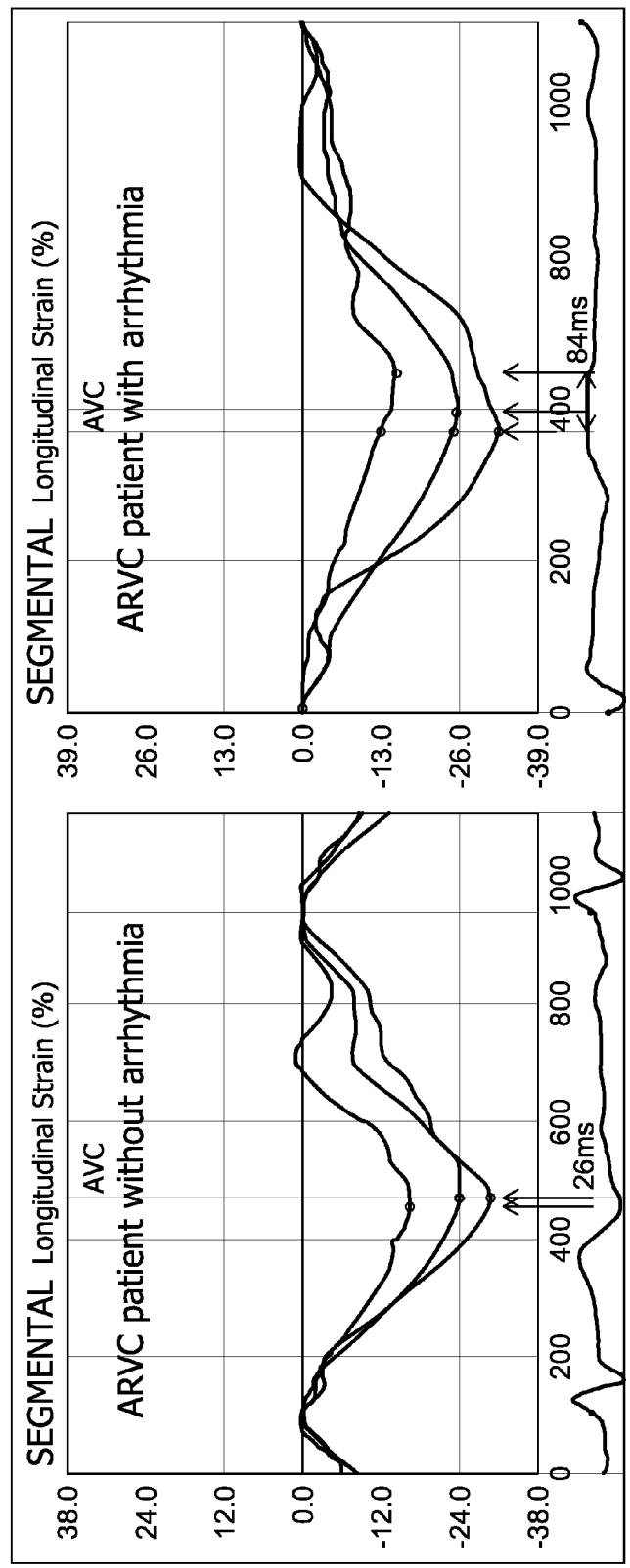

FIG. 9 shows increased mechanical dispersion in an ARVC patient with arrhythmias.

FIG. 10

Figure 10:
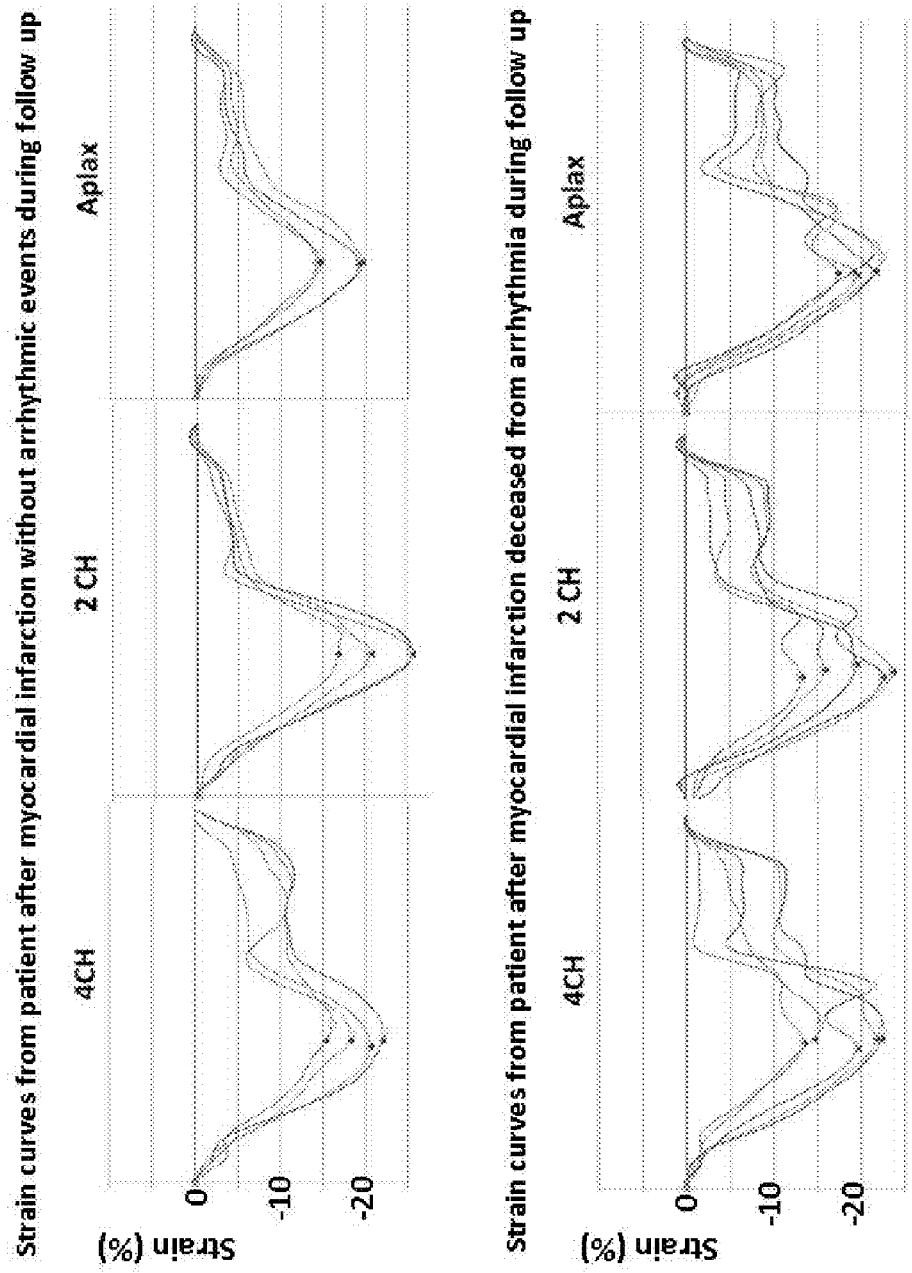

FIG. 10 displays strain curves from 16 left ventricular segments in a patient after myocardial infarction without arrhythmic events (upper panels). Boxes indicate the timing of maximum myocardial shortening of each segment. Timing of maximum myocardial shortening is homogeneous in all curves and mechanical dispersion is 14 ms. Lower panels display strain curves from a patient after myocardial infarction who died from arrhythmias during follow up (lower panels). Timing of maximum myocardial shortening is dispersed and mechanical dispersion is 47 ms. 4CH: apical 4 chamber view, 2 CH: apical 2 chamber view, Aplax: apical long axis view.

The present invention will now be described in more detail in the following.

DETAILED DESCRIPTION OF THE INVENTION

Definitions

Prior to discussing the present invention in further details, the following terms and conventions will first be defined:

Ejection Fraction (EF)

In cardiovascular physiology, ejection fraction (EF) is the fraction of blood pumped out of a ventricle with each heart beat. The term ejection fraction applies to both the right and left ventricles; one can speak equally of the left ventricular ejection fraction (LVEF) and the right ventricular ejection fraction (RVEF).

Primary Cardiomyopathy

Examples of primary cardiomyopathies are Hypertrophic cardiomyopathy (HCM), arrhythmogenic right ventricular cardiomyopathy (ARVC), Left ventricular non-compaction (LVNC), mitochondrial myopathies, dilated cardiomyopathy (DCM), restrictive cardiomyopathy, inflammatory cardiomyopathy, Tako-tsubo cardiomyopathy, peripartum cardiomyopathy and tachycardia induced cardiomyopathy.

In one embodiment of the invention the primary cardiomyopathy is not classified as a Ion Channel Disorder.

In another embodiment of the invention the invention relates to primary cardiomyopathies, with the proviso that the primary cardiomyopathy is not classified as a ion channel disorder.

Myocardial Mechanical Dispersion

Mechanical dispersion is a measure of timing of myocardial contraction. In a normal heart, systolic contractions in different segments of the heart occur relatively simultaneous. Similarly, the duration of myocardial contraction is homogenous throughout the heart. Therefore end of contraction is also homogeneous. In patients with heart disease of different etiologies, start of contraction can be delayed in some regions of the hearts and contraction duration can be prolonged in some regions. End of contraction will therefore be dispersed. These regional differences in timing of myocardial contraction can be assessed by sensitive echocardiographic methods. Homogeneous regional myocardial contraction is defined as mechanical dispersion.

Myocardial mechanical dispersion may be calculated in two different ways:

1) Mechanical dispersion: Standard deviation of time interval from ECG onset Q/onset R wave to maximum myocardial shortening in 16 LV segments. Time interval from ECG onset Q/onset R wave to maximum myocardial shortening may be measured in 16 different parts of the left ventricle. Standard deviation is calculated from these 16 time intervals and reflect the variability of time intervals.

Let X be a random variable with mean value μ:

$$E[X]=\mu$$

Here the operator E denotes the average or expected value of X. Then the standard deviation of X is the quantity $$\sigma=\sqrt{E[(X-\mu)^2]}.$$

That is, the standard deviation a (sigma) is the square root of the average value of $(X-\mu)2$.

In the case where X takes random values from a finite data set $\chi_1, \chi_2, \ldots, \chi_N$, 20 with each value having the same probability, the standard deviation is $$\sigma = \sqrt{\frac{(x_1 - \mu)^2 + (x_2 - \mu)^2 + \ldots + (x_N - \mu)^2}{N}},$$

or, using summation notation, $$\sigma = \sqrt{\frac{1}{N}\sum_{i=1}^{N}(x_i - \mu)^2},$$

2) Delta contraction duration: Difference between segments with longest and shortest time interval from ECG onset Q/onset R wave to maximum myocardial shortening.

The person skilled in the art may use other methods to calculate myocardinal mechanical dispersion. Thus, the above is mere examples of calculation methods.

Global Strain

Global strain may be calculated as the average value of maximum myocardial shortening in 16 LV segments.

Strain (maximum myocardial shortening) is assessed in 16 segments from the left ventricle. Average from these 16 strain values:

Global strain=(strain segment1+strain segment2+ . . . strain segment 16)/16

Abbreviations:
EF=ejection fraction
ECG=electrocardiogram
LV=left ventricle
ICD=implantable cardioverter-defibrillator
CABG=coronary artery bypass graft
MI=myocardial infarction
VT=ventricular tachycardia
VF=ventricular fibrillation
ATP=anti tachycardia pacing
PCI=percutaneous coronary intervention Estimating the Risk for Ventricular Arrhythmias Since the current methods for estimating the risk for ventricular arrhythmias in subjects who has previously suffered a myocardial infarction (MI) are not very reliable, it would be advantageously to implement more reliable predictions methods in the clinic. Thus, one aspect of the invention relates to a method for predicting the risk for ventricular arrhythmias in a subject who has previously suffered a myocardial infarction or in a subject who suffers from a primary cardiomyopathy, said method comprising measuring a myocardial mechanical dispersion in said subject, and estimating a risk for ventricular arrhythmias by comparing said measured myocardial mechanical dispersion to a cut-off value.

By measuring the myocardial mechanical dispersion in a subject a more reliable measure of the risk for ventricular arrhythmias can be obtained. This can e.g. be seen in FIG. 8 showing an increased mechanical dispersion between individuals who suffered ventricular arrhythmias and those who did not. In addition it can be seen in FIG. 8 that measuring mechanical dispersion is a more reliable measure than only measuring the ejection fraction (EF) which is the method often used in the clinic.

Areas of the Heart

The mechanical dispersion may be measured at different areas of the heart. Thus, in an embodiment the mechanical dispersion is measured on at least one of the left ventricle and the right ventricle. In patients after myocardial infarction, left ventricle measurements are most important. In other patients with other heart muscle diseases, e.g. patients with right sided cardiomyopathies it would make sense to measure even in both ventricles. In another embodiment the mechanical dispersion is measured on the left ventricle.

Primary Cardiomyopathies

Different groups of patients or subjects may be tested according to the method according to the invention. Thus, in an embodiment the primary cardiomyopathies are selected from the group consisting of Hypertrophic cardiomyopathy (HCM), arrhythmogenic right ventricular cardiomyopathy (ARVC), Left ventricular non-compaction (LVNC), mitochondrial myopathies, dilated cardiomyopathy (DCM), restrictive cardiomyopathy, inflammatory cardiomyopathy, Tako-tsubo cardiomyopathy, peripartum cardiomyopathy and tachycardia induced cardiomyopathy.

In one embodiment of the invention the primary cardiomyopathy is not classified as a Ion Channel Disorder. In another embodiment of the invention, the invention relates to primary cardiomyopathies, with the proviso that the primary cardiomyopathy is not classified as a ion channel disorder.

Strain

The myocardial mechanical dispersion may be measured in different ways. Thus, in on embodiment the invention relates to a method further comprising measuring strain in a plurality of left ventricular muscle segments in said subject, and determining a measure of myocardial mechanical dispersion from said strain measurements. This method can predict arrhythmias even in patients with relatively small myocardial infarctions and other heart muscle diseases with minor tissue heterogeneity. Therefore these patients can be evaluated for lifesaving ICD therapy. Current guidelines for ICD therapy is based on EF and only patients with EF<35% (significantly reduced cardiac function) are evaluated for ICD therapy. The largest proportion of patients who die after MI today have EF>35% and therefore were not evaluated for ICD therapy.

Left Ventricular Ejection Fraction

Combining different measurements may result in more reliable estimates of the risk for ventricular arrhythmias. Thus in an embodiment the invention relates to a method further comprising measuring the left ventricular ejection fraction in said subject. Since measuring the left ventricular ejection fraction is a standard measuring method it may be advantageously to combine different measurements to obtain more reliable results.

Echocardiography, MRI and CT

The myocardial mechanical dispersion may be measured using different equipment and methods. Thus, in an embodiment the invention relates to a method, wherein the myocardial mechanical dispersion and strain are measured by a method selected from the group consisting of echocardiography, MRI and CT techniques.

Calculation of Mechanical Dispersion

The way the myocardial mechanical dispersion is calculated may be performed in different ways. Thus, in another embodiment the invention relates to a method, wherein the myocardial mechanical dispersion is calculated as standard deviation of time to maximum myocardial shortening or delta contraction duration for each muscle segment as determined from the strain measurements. Standard deviation from 16 cardiac segments is a robust measure of variability of time to maximum myocardial shortening. One inaccurate measurement has minor impact on the final value of mechanical dispersion calculated as standard deviation. The number of segments analyzed may vary depending on the specific assay. Thus, in an embodiment 5-30 segments, such as 10-30 segments or such as 10-20 segments are analyzed.

Mechanical dispersion calculated as delta contraction duration is simply the difference between longest and shortest of the 16 measured times to maximum myocardial shortening. This parameter is easy to calculate and therefore faster to obtain. As above, the number of segments analyzed may vary depending on the specific assay. Thus, in an embodiment 5-30 segments, such as 10-30 segments or such as 10-20 segments are analyzed.

Mechanical Dispersion Values

When the risk is to be estimated both specificity and the sensitivity of the assay has to be taken into account. Thus, in yet an embodiment the invention relates to a method, wherein a myocardial mechanical dispersion above 70 ms is indicative of the subject being at risk for ventricular arrhythmias, with the proviso that mechanical dispersion is calculated as standard deviation of time to maximum myocardial shortening.

Figure 3:
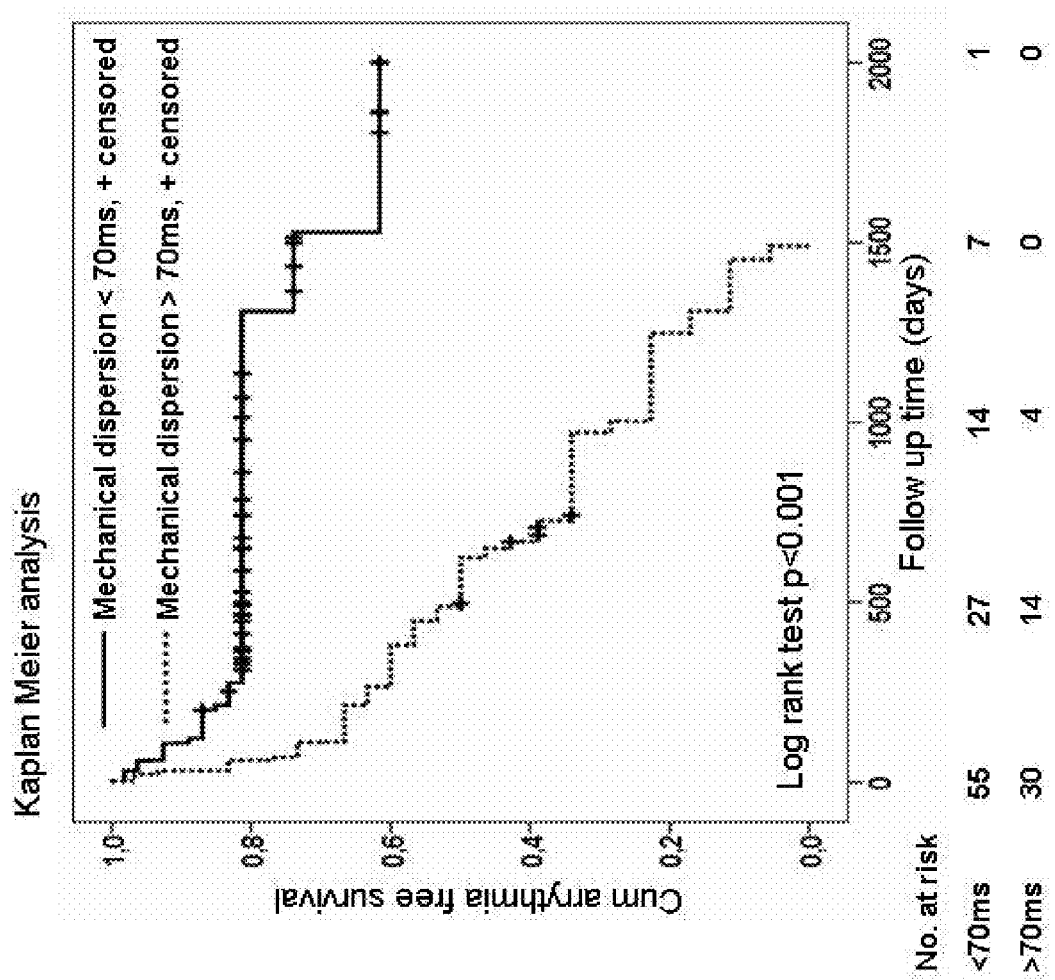
Figure 4:
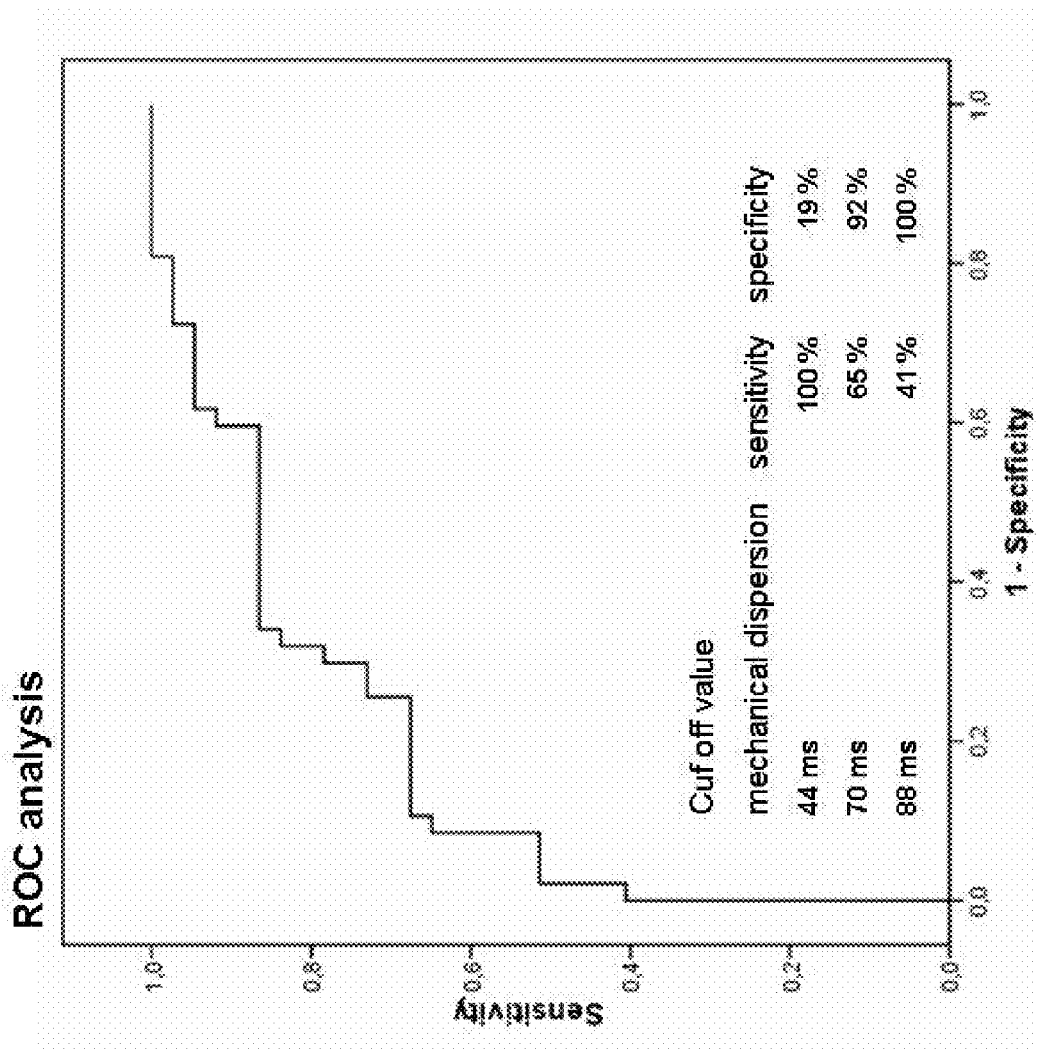

The put in cut-off value will depend on the sensitivity and specificity desired for a specific assay. FIGS. 3 and 4 show different plots illustrating sensitivity and specificity of the method according to the invention. It can be seen that a cut-off value of 70 ms provides both a high sensitivity and specificity.

Other values may also be desirable. Thus, in an embodiment the invention relates to a method wherein a myocardial mechanical dispersion above 30 ms is indicative of the subject being at risk for ventricular arrhythmias, with the proviso that mechanical dispersion is calculated as standard deviation of time to maximum myocardial shortening such as a myocardial mechanical dispersion above 40 ms, such as above 50 ms, such as above 60 ms, such as above 80 ms such as above 90 ms such as above 100 ms. The exact choice of value may depend on information of the subject such as gender, age, and medical history. Furthermore, the myocardial mechanical dispersion may be calculated by different algorithms based on data from different imaging modalities. As the quantification of myocardial mechanical dispersion depends on the used approach, the value of the cut-off value preferably depends on how the myocardial mechanical dispersion is measured and/or calculated.

In another embodiment a myocardial mechanical dispersion above 220 ms is indicative of the subject being at risk for ventricular arrhythmias, with the proviso that mechanical dispersion is calculated as delta contraction duration. For mechanical dispersion calculated as delta contraction duration a value of 220 ms gives 76% sensitivity and 81% specificity for cardiac arrhythmias and is defined as the optimal cut-off value. As above, the put in a cut-off value will depend on the sensitivity and specificity desired for a specific assay. Thus, in an embodiment the invention relates to a method wherein a myocardial mechanical dispersion above 180 ms is indicative of the subject being at risk for ventricular arrhythmias, with the proviso that mechanical dispersion is calculated as delta contraction duration such as a myocardial mechanical dispersion above 150 ms, such as above 180 ms, such as above 200 ms such as above 240 ms such as above 260 ms or such as above 280 ms. The exact choice of value may depend on information of the subject such as gender, age, and medical history. Furthermore, the myocardial mechanical dispersion may be calculated by different algorithms based on data from different imaging modalities. As the quantification of myocardial mechanical dispersion depends on the used approach, the value of the cut-off value preferably depends on how the myocardial mechanical dispersion is measured and/or calculated.

Determining the Type of Therapy

Besides only determining the risk for ventricular arrhythmias, the method may also be used in for determining a type of therapy. Thus, in another aspect, the invention relates to a method for estimating evaluating whether a subject who has previously suffered a myocardial infarction or evaluating whether a subject who suffers from a primary cardiomyopathy is a candidate for implantable cardioverter-defibrillator (ICD) therapy, said method comprising measuring a myocardial mechanical dispersion in said subject, and estimating a risk for ventricular arrhythmias by comparing said measured myocardial mechanical dispersion to a cut-off value .

Areas of the Heart

The mechanical dispersion may be measured at different areas of the heart. Thus, in an embodiment the mechanical dispersion is measured on at least one of the left ventricle and the right ventricle. In patients after myocardial infarction, left ventricle measurements are most important. In other patients with other heart muscle diseases, e.g. patients with right sided cardiomyopathies it would make sense to measure even in both ventricles. In another embodiment the mechanical dispersion is measured on the left ventricle.

Primary Cardiomyopathies

Different groups of patients or subjects may be tested according to the method according to the invention. Thus, in an embodiment the primary cardiomyopathies are selected from the group consisting of Hypertrophic cardiomyopathy (HCM), arrhythmogenic right ventricular cardiomyopathy (ARVC), Left ventricular non-compaction (LVNC), mitochondrial myopathies, dilated cardiomyopathy (DCM), restrictive cardiomyopathy, inflammatory cardiomyopathy, Tako-tsubo cardiomyopathy, peripartum cardiomyopathy and tachycardia induced cardiomyopathy. In one embodiment of the invention the primary cardiomyopathy is not classified as a Ion Channel Disorder. In another embodiment of the invention, the invention relates to primary cardiomyopathies, with the proviso that the primary cardiomyopathy is not classified as a ion channel disorder.

Strain

The myocardial mechanical dispersion may be measured in different ways. Thus, in on embodiment the invention relates to a method further comprising measuring strain in a plurality of left ventricular muscle segments in said subject, and determining a measure of myocardial mechanical dispersion from said strain measurements. This method can predict arrhythmias even in patients with relatively small myocardial infarctions and other heart muscle diseases with minor tissue heterogeneity. Therefore these patients can be evaluated for lifesaving ICD therapy. Current guidelines for ICD therapy is based on EF and only patients with EF<35% (significantly reduced cardiac function) are evaluated for ICD therapy. The largest proportion of patients who die after MI today have EF>35% and therefore were not evaluated for ICD therapy.

Left Ventricular Ejection Fraction

Combining different measurements may result in more reliable estimates of the risk for ventricular arrhythmias. Thus in an embodiment the invention relates to a method further comprising measuring the left ventricular ejection fraction in said subject. Since measuring the left ventricular ejection fraction is a standard measuring method it may be advantageously to combine different measurements to obtain more reliable results.

Echocardiography, MRI and CT

The myocardial mechanical dispersion may be measured using different equipment and methods. Thus, in an embodiment the invention relates to a method, wherein the myocardial mechanical dispersion and strain are measured by a method selected from the group consisting of echocardiography, MRI and CT techniques.

Calculation of Mechanical Dispersion

The way the myocardial mechanical dispersion is calculated may be performed in different ways. Thus, in another embodiment the invention relates to a method, wherein the myocardial mechanical dispersion is calculated as standard deviation of time to maximum myocardial shortening or delta contraction duration for each muscle segment as determined from the strain measurements. Standard deviation from 16 cardiac segments is a robust measure of variability of time to maximum myocardial shortening. One inaccurate measurement has minor impact on the final value of mechanical dispersion calculated as standard deviation. The number of segments analyzed may vary depending on the specific assay. Thus, in an embodiment 5-30 segments, such as 10-30 segments or such as 10-20 segments are analyzed.

Mechanical dispersion calculated as delta contraction duration is simply the difference between longest and shortest of the 16 measured times to maximum myocardial shortening. This parameter is easy to calculate and therefore faster to obtain. As above, the number of segments analyzed may vary depending on the specific assay. Thus, in an embodiment 5-30 segments, such as 10-30 segments or such as 10-20 segments are analyzed.

Mechanical Dispersion Values

When the risk is to be estimated both specificity and the sensitivity of the assay has to be taken into account. Thus, in yet an embodiment the invention relates to a method, wherein a myocardial mechanical dispersion above 70 ms is indicative of the subject being at risk for ventricular arrhythmias, with the proviso that mechanical dispersion is calculated as standard deviation of time to maximum myocardial shortening.

The put in a cut-off value will depend on the sensitivity and specificity desired for a specific assay. FIGS. 3 and 4 show different plots illustrating sensitivity and specificity of the method according to the invention. It can be seen that a cut-off value of 70 ms provides both a high sensitivity and specificity. Other values may also be desirable. Thus, in an embodiment the invention relates to a method wherein a myocardial mechanical dispersion above 30 ms is indicative of the subject being at risk for ventricular arrhythmias, with the proviso that mechanical dispersion is calculated as standard deviation of time to maximum myocardial shortening such as a myocardial mechanical dispersion above 40 ms, such as above 50 ms, such as above 60 ms, such as above 80 ms such as above 90 ms such as above 100 ms. The exact choice of value may depend on information of the subject such as gender, age, and medical history. Furthermore, the myocardial mechanical dispersion may be calculated by different algorithms based on data from different imaging modalities. As the quantification of myocardial mechanical dispersion depends on the used approach, the value of the cut-off value preferably depends on how the myocardial mechanical dispersion is measured and/or calculated.

In another embodiment a myocardial mechanical dispersion above 220 ms is indicative of the subject being at risk for ventricular arrhythmias, with the proviso that mechanical dispersion is calculated as delta contraction duration. For mechanical dispersion calculated as delta contraction duration a value of 220 ms gives 76% sensitivity and 81% specificity for cardiac arrhythmias and is defined as the optimal cut of value. As above, the put in a cut-off value will depend on the sensitivity and specificity desired for a specific assay. Thus, in an embodiment the invention relates to a method wherein a myocardial mechanical dispersion above 180 ms is indicative of the subject being at risk for ventricular arrhythmias, with the proviso that mechanical dispersion is calculated as delta contraction duration such as a myocardial mechanical dispersion above 150 ms, such as above 180 ms, such as above 200 ms such as above 240 ms such as above 260 ms or such as above 280 ms. The exact choice of value may depend on information of the subject such as gender, age, and medical history. Furthermore, the myocardial mechanical dispersion may be calculated by different algorithms based on data from different imaging modalities. As the quantification of myocardial mechanical dispersion depends on the used approach, the value of the cut-off value preferably depends on how the myocardial mechanical dispersion is measured and/or calculated.

Echocardiography System

A general system for determining whether a subject is a candidate for implantable cardioverter-defibrillator (ICD) therapy may be advantageously. Thus, in yet an aspect the invention relates to the use of an echocardiography system on a subject who has previously suffered a myocardial infarction (MI) or on a subject who suffers from a primary cardiomyopathy for determining whether the subject is a candidate for implantable cardioverter-defibrillator (ICD) therapy, comprising the use of the apparatus for measurement of strain in a plurality of left ventricular segments of the subject, and for determining a measure of mechanical myocardial dispersion from the measured strains. As previously described both MRI and CT may be used to perform such measurements.

It may be advantageous if the system was able to evaluate the measurements in respect to predefined threshold values. Thus in an embodiment the system further comprises using the echocardiography system to provide a comparison of the determined measure with a predefined threshold value. Such threshold values may be determined by ROC curves or similar as described in the present text.

The system according to the invention be comprise different parts to make the system functional. Thus, in an embodiment the invention relates to a echocardiography system comprising an echocardiography apparatus, a user terminal and software for determining the measure of myocardial mechanical dispersion from the measured strains.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1

Methods
Study Population

A total of 85 post-MI patients fulfilling indications for ICD therapy were recruited from 4 university hospitals (St. Olays Hospital, Trondheim, Ullevål University Hospital, Oslo, University Hospital Gasthuisberg, Leuven and Rikshospitalet University Hospital, Oslo). All patients were included prospectively with echocardiographic examination in general performed during the hospitalization for ICD implantation (median 0(-175, 84) days). Inclusion criteria were prior hospitalization due to myocardial infarction and indication for ICD therapy according to primary or secondary prevention criteria. Primary prevention criteria (n=44) included patients with EF<35% at least 40 days post-MI or EF<40% and non-sustained ventricular tachycardia (nsVT) and sustained arrhythmia inducible in electrophysiology study. Secondary prevention criteria (n=41) included cardiac arrest survivors and patients with sustained VT. In secondary prevention patients, the arrhythmia (VT or VF) which provided the indication for ICD therapy was defined as index arrhythmia. Medical treatment and revascularization therapy were recorded. Exclusion criteria were atrial fibrillation, left bundle branch block, previous coronary artery bypass graft (CABG) surgery and valve regurgitations greater than moderate. No patients had more than mild valvular stenoses. Arrhythmic events during follow up were defined as ventricular arrhythmias that required appropriate anti tachycardia pacing (ATP) or shock from the ICD. Time from ICD implantation to first arrhythmic event during follow up was recorded. Follow up time after ICD implantation was minimum 300 days.

All 85 ICD patients underwent coronary angiography before ICD implantation. Percutaneous coronary intervention (PCI) was performed in 49 patients. Four patients underwent CABG surgery after inclusion and ICD implantation. One patient had received thrombolytic therapy for myocardial infarction and had no significant stenoses at coronary angiography. In 31 patients the coronary lesions were ineligible for revascularization.

Control Groups

From our outpatient clinic we recruited 20 patients with prior hospitalization due to MI. Exclusion criteria were identical to the study population. None of these had arrhythmic events.

The control group consisted of 23 healthy individuals and was recruited from the hospital staff. All had normal ECG and echocardiography.

ECG

Twelve lead ECG was obtained in all participants. The QT-interval was heart rate corrected with Bazett's formula.

Written informed consent was given by all participants. The study was approved by the Regional Committee for Medical Research Ethics.

Echocardiography

The echocardiographic studies were performed using Vivid 7 (GE, Horten, Norway) and analyzed with software (EchoPAC®, GE). LVEF was assessed ad modum Simpson. Myocardial strain measurements were performed using speckle tracking echocardiography. Longitudinal strain was obtained from all apical views at 63±23 frames/s. Global LV longitudinal strain was obtained by averaging maximum systolic shortening in a 16 segments model (FIG. 1). Post systolic shortening was not included in global strain analyses. Maximum systolic lengthening was recorded in segments where no shortening was present.

Myocardial Mechanical Dispersion

Time to maximum myocardial shortening, including post systolic shortening if present, was measured from the ECG onset Q/onset R wave in 16 LV segments (FIG. 1). Inclusion of an infarcted segment in time analyses required approval from the automated software. The maximum myocardial shortening from a representative strain curve with a shortening duration of minimum 50 ms was used in the time analyzes. Segments where no shortening was present were excluded.

To quantify LV mechanical dispersion we used:

1) Standard deviation of the 16 different time intervals to maximum myocardial shortening in each participant. This parameter was defined as mechanical dispersion.
2) An alternative measure for mechanical dispersion was the difference between the longest and the shortest time interval from ECG onset Q/onset R wave to maximum myocardial shortening in each individual. This parameter was defined as delta contraction duration.

Strain parameters could be assessed in 95% of the myocardial segments in the study group and in 91% of the subjects in the control group. Time measurements included 88% of the segments in the infarcted patients with ICD. The intra observer analysis was done blinded to patients' arrhythmia outcome status.

Statistical Analyses

Data were presented as mean ±standard deviation or as median (range). Comparisons of means were analyzed by ANOVA with the Bonferroni correction for multiple comparisons (SPSS 15.0). Kruskal Wallis test was performed for non-parametric variables. Proportions were compared with the use of Chi square test. Cox regression analysis was used in the patient population to identify predictors of the outcome arrhythmia requiring appropriate ICD treatment. Patients with ICD due to primary and secondary prevention criteria were analyzed separately. Hazard ratios and 95% confidence intervals (CI) were calculated. The multivariate analysis was performed by including significant variables from the univariate model ($p<0.05$) in addition to age and EF which were forced in. A close relationship was observed between mechanical dispersion and delta contraction duration and therefore only dispersion was included in the multivariate analysis. Kaplan-Meier analysis was used to create freedom-from-arrhythmia survival curves. The value closest to the upper left corner of the ROC curve determined optimal sensitivity and specificity for the ability of mechanical dispersion to identify arrhythmic events. Reproducibility was expressed as intraclass correlation coefficient. P-values less than 0.05 were considered significant.

Results

Clinical Findings

Clinical data are presented in FIG. 5. Indication for ICD therapy according to primary prevention criteria was present in 44 and secondary prevention in 41 patients. Thirty-eight ICD patients experienced one or more episodes with sustained VT or VF requiring appropriate ICD therapy (ATP or shock) while 47 ICD patients had no sustained arrhythmia during 2.3(0.6,5.5) years follow up. The duration of QRS, QTc and use of medication were similar in the two ICD groups (FIG. 5). Median time from ICD implantation to first ICD therapy was 239 (2,1529) days.

Among the 38 patients with recorded arrhythmias during follow up, 30 received ICD therapy due to VT, 5 due to VF and for unknown reason in 3 patients. A coronary angiography was performed in 4 of the 5 patients with VF during follow up and 3 required PCI due to new coronary lesions. Arrhythmias occurred later during follow up in patients with ICD therapy due to VF compared to those with VT (2.6 years vs. 1.0 years, p=0.02). There were no differences in QRS and QTc duration or in echocardiographic parameters between patients with VF or VT during follow up.

No differences were found between the revascularized and non-revascularized patients regarding incidence or modality of arrhythmia (VT or VF) as recorded from the ICD device (p=0.70). Revascularized patients had significantly better EF compared to non-revascularized patients (EF 37±11% vs. 32±8%, p=0.04).

Primary Prevention Patients

In patients with primary prevention (n=44), 12 were implanted on indication EF<35% and 32 had EF<40%, nsVT and were inducible in electrophysiology study. 15 of the 32 with nsVT had EF<35%. During follow up there were significantly more arrhythmic events in those with EF<40% and nsVT/inducible (18 of 32 patients) compared to those with EF<35% (2 of 12 patients) (p=0.02). Primary prevention patients with ICD indication EF<35% alone had less arrhythmic events during follow up compared to all other patients (p=0.04). Positive and negative predictive values for later arrhythmias were 17% and 43%, respectively, when ICD implantation was based on EF alone.

Secondary Prevention Patients

In secondary prevention patients (n=41), 15 patients had EF<35% and 36 EF>35% (FIG. 6). All of these had experienced a sustained VT or were cardiac arrest survivors. The index arrhythmia was VT in 24 and VF in 17 patients. The probability of later arrhythmias was similar regardless if index arrhythmia was VT or VF (p=0.12). 44% experienced arrhythmic events during follow up.

Myocardial Mechanical Dispersion

Both methods for quantification of mechanical dispersion were related to the occurrence of arrhythmic events. Standard deviation of time to maximum myocardial shortening was significantly longer in those with arrhythmias (p<0.001) (FIG. 6 and FIG. 2). In addition, delta contraction duration (time difference between segments with the longest and the shortest duration of systolic shortening) was prolonged in the arrhythmic ICD patients compared to the non arrhythmic (p<0.001) (FIG. 6). Univariate analyses of risk factors for ventricular arrhythmias that required appropriate ICD therapy are shown in FIG. 7. In the multivariate analysis, mechanical dispersion was a strong and independent predictor of arrhythmias (p<0.001). Mechanical dispersion was more pronounced in patients with EF>35% who experienced arrhythmia (n=22) compared to those without arrhythmias (n=21) (p=0.01) (FIG. 8). In patients with ICD due to EF indication alone, 2 of 12 had arrhythmias during follow up. Importantly, both these patients had mechanical dispersion >70 ms (138 ms and 142 ms, respectively). In patients with ICD due to EF indication alone and without further arrhythmic events (n=10), mechanical dispersion was significantly lower compared to the rest of the patients who all had experienced arrhythmic events before or after ICD implantation (50±15 ms vs. 71±26 ms, p=0.01). FIG. 3 shows a Kaplan Meier plot that demonstrates arrhythmia event free survival in the ICD population. ICD patients with mechanical dispersion >70 ms showed more frequent arrhythmic events than ICD patients with dispersion <70 ms (Log Rank test, p<0.001). A mechanical dispersion of 70 ms showed sensitivity of 65% (95% CI 0.55-0.71) and specificity of 92% (95% CI 0.83-0.96) for identifying arrhythmic events (FIG. 4).

Control patients with prior MI without any arrhythmias had significantly lower mechanical dispersion compared to ICD patients with arrhythmias during follow up (p<0.001). Compared to ICD patients without arrhythmic events during follow up control patients with prior MI had lower mechanical dispersion even though not reaching significant levels (p=0.11) (FIG. 6). Healthy individuals had shorter and more homogeneous time measurements compared with all post-MI groups (FIG. 6).

LV Volumes and Function

Importantly, EF and LV volumes were equal in the ICD groups and could not separate between those with recurrent arrhythmias and those without (FIG. 6). Global strain was not reduced in patients with follow up arrhythmias compared to those without in the total study population. When analyzed separately in patients with EF<35% and EF>35%, global strain was significantly reduced in patients with arrhythmias (FIG. 8).

Intra observer and inter observer variability were 0.98 and 0.98, respectively, for strain measurements and 0.86 and 0.81 for time measurements.

Discussion

This study introduces a new principle in risk assessment for life threatening arrhythmias in patients with a previous myocardial infarction. Patients with recorded arrhythmias showed greater mechanical dispersion by standard deviation of time to maximum myocardial shortening and delta contraction duration. Mechanical dispersion was a strong and independent predictor of arrhythmic evens. Our findings support the idea that electrical abnormalities in post-MI patients are associated with mechanical dispersion. EF by echocardiography was not able to discriminate post-MI patients with respect to arrhythmic events, neither in primary or secondary prevention patients. Global strain, however, provided added value in arrhythmia risk stratification.

Mechanical Dispersion

There is ample evidence from different cardiac disease models, including heart failure, ischemia and infarction that increases in dispersion of conduction velocity result in susceptibility to arrhythmias. These electrical abnormalities will presumptively lead to changes in myocardial function, as shown in our study. Assessing the extent of electrical dispersion in the individual patient has so far been difficult. A recent study has shown that tissue heterogeneity in post-MI patients assessed by MRI correlated with increased susceptibility to ventricular arrhythmias induced by programmed ventricular stimulation. Our study supports the idea that tissue heterogeneity, leading to a dispersed myocardial contraction, is associated with risk of arrhythmic events.

In control post-MI patients with preserved EF, mechanical dispersion was significantly lower compared to ICD patients with recorded arrhythmias, and tended to be lower compared to ICD patients without arrhythmic events. These findings demonstrate presence of mechanical dispersion in all post-MI patients and support the assumption that the extent of mechanical dispersion is important for arrhythmogenesis.

LV Function

The relationship between left ventricular systolic dysfunction and deaths due to progressive heart failure and ventricular arrhythmias in patients post-MI is well established Earlier echocardiographic studies have observed that an EF of 40% serves as the threshold for identifying high-risk individuals. However, EF has reduced sensitivity in predicting sudden death; less than 50% of patients with prior MI who die suddenly have EF below 30%.

Myocardial strain assessed by speckle tracking echocardiography represents a novel technique to quantify LV function. Strain measures LV contraction. Speckle based strain has shown to be a robust technique for assessment of LV function. A recent study has demonstrated that speckle tracking strain is superior to EF for assessment of myocardial function post-MI. In our study, global strain was decreased in post-MI patients with EF>35% and arrhythmic events. This finding might suggest that global strain might become a useful tool for risk stratification in post-MI patients with relatively preserved LV function. EF, however, failed to identify arrhythmic events in our post-MI patients with EF>35%.

Clinical Implications

Measurements of mechanical dispersion and global strain in post-MI patients add important information about risk of arrhythmia beyond EF. Importantly, in patients with preserved or slightly reduced EF, mechanical dispersion above 70 ms identified post-MI patients with increased risk of life threatening arrhythmias. According to current guidelines for primary prevention, post-MI patients with EF<35% should be considered for ICD therapy. The novel principles presented in this study might be useful to identify risk of arrhythmias in post-MI patients with relatively preserved EF who do not fulfil current ICD indications (EF<35%). Future trials should investigate if mechanical dispersion and global strain can be used to select additional patients for ICD therapy among the majority of post-MI patients with relatively preserved EF in whom current ICD indications fail. The proposed echocardiographic measurements can be easily implemented in clinical routine.

Limitations

Our study shows that mechanical dispersion is associated with ventricular arrhythmia. Whether mechanical dispersion can be explained by electrical dispersion has to be studied experimentally.

Clinical implications of these novel methods must be interpreted with respect to the fact that all patients fulfilled current guidelines for ICD therapy. The present study was not designed to find the optimal clinical cutoff value for mechanical dispersion in patients not fulfilling current ICD indications.

Conclusions

This study demonstrates that post-MI patients at risk for cardiac arrhythmias have increased myocardial mechanical dispersion. Assessment of mechanical dispersion by echocardiography might therefore help identifying post-MI patients susceptible to ventricular arrhythmias beyond the extent of reduced LV function. Global strain may become an additional tool for risk stratification in post-MI patients with relatively preserved ventricles.

Example 2

Right ventricular mechanical dispersion predicts malignant arrhythmias in patients with Arrhytmogenic Right Ventricular Cardiomyopathy (ARVC).

Purpose

Mechanical dispersion (heterogeneous contraction) can be assessed by strain echocardiography and may reflect electrical dispersion. We hypothesized that mechanical dispersion by myocardial strain can predict risk for ventricular arrhythmia in patients with ARVC.

Methods: We included 50 patients with ARVC diagnosis based on clinical criteria proposed by the European Society of Cardiology or genetic mutation criteria. ARVC related mutations (27 PKP2 & 5 DSP) were confirmed in 32 patients and 18 were mutation negative. Ventricular arrhythmia was documented in 37 patients.

Strain was assessed by speckle tracking echocardiography. Contraction duration was measured as time from start Ron ECG to maximum RV shortening by strain. Standard deviation (SD) of contraction duration was calculated as a parameter of mechanical dispersion, in a 3 RV segment model.

Results

Patients with arrhythmias showed increased RV mechanical dispersion compared to those without (45±33 ms vs 14±9 ms, p=0.004). RV mechanical dispersion (per 10 ms increase) was a predictor of arrhythmias in a multivariate regression analysis with OR 2.7(95% CI 1.2-6.0), p=0.01. RV strain was −20±6% vs−24±5%, p=0.12. FIG. 9 shows increased mechanical dispersion in an ARVC patient with arrhythmias.

Conclusions

RV mechanical dispersion assessed by strain was more pronounced in ARVC patients with arrhythmias. Increased RV mechanical dispersion predicted ventricular arrhythmias in ARVC patients independently of RV function.

Example 3

Patient Example

The method of mechanical dispersion will be applied on patients after myocardial infarction in a prospective multi center trial. In all 1100 patients are planned for inclusion to evaluate if the method can predict arrhythmic events in the large proportion of patients after myocardial infarction. Preliminary results from this study are promising (see FIG. 10).

The invention claimed is:

1. A method for predicting the risk for ventricular arrhythmias, said method comprising:
    selecting a subject who has previously suffered a myocardial infarction or a subject who suffers from a primary cardiomyopathy;
    measuring a myocardial mechanical dispersion in said subject,
    estimating a risk for ventricular arrhythmias by comparing said measured myocardial mechanical dispersion to a cut-off value, and
    classifying the subject as in need of implantable cardioverter-defibrillator therapy based on the estimated risk for ventricular arrhythmias.

2. The method according to claim 1, wherein the mechanical dispersion is measured on at least one of the left ventricle and the right ventricle.

3. The method according to claim 1, wherein the mechanical dispersion is measured on the left ventricle.

4. The method according to claim 1, wherein the primary cardiomyopathies are selected from the group consisting of Hypertrophic cardiomyopathy (HCM), arrhythmogenic right ventricular cardiomyopathy (ARVC), Left ventricular non-compaction (LVNC), mitochondrial myopathies, dilated cardiomyopathy (DCM), restrictive cardiomyopathy, inflammatory cardiomyopathy, Tako-tsubo cardiomyopathy, peripartum cardiomyopathy and tachycardia induced cardiomyopathy.

5. The method according to claim 1, further comprising measuring strain in a plurality of left ventricular muscle segments in said subject, and determining a measure of myocardial dispersion from said strain measurements.

6. The method according to claim 1, further comprising measuring the left ventricular ejection fraction in said subject.

7. The method according to claim 1, wherein a myocardial mechanical dispersion above 50 ms is indicative of the subject being at risk for ventricular arrhythmias, with the proviso that mechanical dispersion is calculated as standard deviation of time to maximum myocardial shortening.

8. The method according to claim 1, wherein a myocardial mechanical dispersion above 200 ms is indicative of the subject being at risk for ventricular arrhythmias, with the proviso that mechanical dispersion is calculated as delta contraction duration.

9. A method for evaluating whether a subject is a candidate for implantable cardioverter-defibrillator (ICD) therapy, said method comprising:
   selecting a subject who has previously suffered a myocardial infarction or a subject who suffers from a non-ischemic cardiomyopathy;
   measuring a myocardial mechanical dispersion in said subject,
   estimating a risk for ventricular arrhythmias by comparing said measured myocardial mechanical dispersion to a cut-off value, and
   classifying the subject as in need of implantable cardioverter-defibrillator therapy based on the estimated risk for ventricular arrhythmias.

10. The method according to claim 9, wherein the mechanical dispersion is measured on at least one of the left ventricle and the right ventricle.

11. The method according to claim 9, wherein the mechanical dispersion is measured on the left ventricle.

12. The method according to claim 9, wherein the primary cardiomyopathies are selected from the group consisting of Hypertrophic cardiomyopathy (HCM), arrhythmogenic right ventricular cardiomyopathy (ARVC), Left ventricular non-compaction (LVNC), mitochondrial myopathies, dilated cardiomyopathy (DCM), restrictive cardiomyopathy, inflammatory cardiomyopathy, Tako-tsubo cardiomyopathy, peripartum cardiomyopathy and tachycardia induced cardiomyopathy.

13. The method according to claim 9, further comprising measuring the strain in a plurality of left ventricular muscle segments in said subject, and determining a measure of myocardial dispersion from said strain measurements.

14. The method according to claim 9 further comprising measuring the left ventricular ejection fraction in said subject.

15. The method according to claim 9, wherein a myocardial mechanical dispersion above 50 ms is indicative of the subject should be further evaluated for implantable cardioverter-defibrillator (ICD) therapy, with the proviso that mechanical dispersion is calculated as standard deviation of time to maximum myocardial shortening.

16. The method according to claim 9, wherein a myocardial mechanical dispersion above 200 ms is indicative of the subject should be further evaluated for implantable cardioverter-defibrillator (ICD) therapy, with the proviso that mechanical dispersion is calculated as delta contraction duration.

17. A method of using of an echocardiography system on a subject for determining whether the subject is a candidate for implantable cardioverter-defibrillator (ICD) therapy, comprising selecting a subject who has previously suffered a myocardial infarction MI or a subject who suffers from a primary cardiomyopathy, using said echocardiography system for a measurement of strain in a plurality of left ventricular segments of the subject, determining a measure of mechanical myocardial dispersion from the measured strains estimating a risk for ventricular arrhyhmias b comparing said measured myocardial mechanical dispersion to a cut-off value, and classifying the subject as in need of implantable cardioverter-defibrillator therapy based on the estimated risk for ventricular arrhythmias.

18. The method according to claim 17, further comprising using the echocardiography system to provide a comparison of the determined measure with a predefined threshold value.

19. The method according to claim 17, wherein the echocardiography system comprises an echocardiography apparatus, a user terminal and software for determining the measure of myocardial mechanical dispersion from the measured strains.

* * * * *